United States Patent [19]
Harris et al.

[11] Patent Number: 5,849,544
[45] Date of Patent: Dec. 15, 1998

[54] AMPLIFICATION AND DETECTION PROCESS

[75] Inventors: Raymond John Harris, Adelaide; Charles Phillip Morris, North Adelaide, both of Australia

[73] Assignees: University of Australia; Adelaide Children's Hospital

[21] Appl. No.: 374,764

[22] PCT Filed: Jul. 26, 1993

[86] PCT No.: PCT/AU93/00379

§ 371 Date: Jan. 24, 1995

§ 102(e) Date: Jan. 24, 1995

[87] PCT Pub. No.: WO94/02634

PCT Pub. Date: Feb. 3, 1994

[30] Foreign Application Priority Data

Jul. 24, 1992 [AU] Australia ............... PL 3705

[51] Int. Cl.$^6$ ............... C12P 19/34; C12Q 1/68
[52] U.S. Cl. ............... 435/91.2; 435/6
[58] Field of Search ............... 435/5, 6, 91.2; 935/77, 78

[56] References Cited

U.S. PATENT DOCUMENTS

| | | | |
|---|---|---|---|
| 5,232,829 | 8/1993 | Longiarv et al. | 435/6 |
| 5,635,347 | 6/1997 | Link et al. | 435/6 |

OTHER PUBLICATIONS

Heller et al, J. Clin, Microbiol. 29:638–641 (1991).
Sanger et al, PNAS 74: 5463–5467 (1977).

*Primary Examiner*—Eggerton A. Campbell
*Attorney, Agent, or Firm*—Brown, Martin, Haller & McClain, LLP

[57] ABSTRACT

This method for detecting a target nucleic acid sequence involves amplification and detection in the same vessel and comprises: (a) amplification of the target nucleic sequence in a vessel which is provided with a solid phase capture probe comprising a nucleic acid sequence capable of hybridizing to at least a portion of said amplified target nucleic acid sequence, said capture probe being incapable of participating or not participating in standard nucleic acid sequence amplification processes, (b) bringing a sample suspected of comprising said target nucleic acid sequence into contact with said capture probe under conditions which allow said amplified target nucleic acid sequence to be bound by said capture probe, and (c) detecting the presence of bound target nucleic acid sequence. In a further aspect, the present invention provides an assay system or kit, for detecting a target nucleic acid sequence in a sample suspected of comprising said target nucleic acid sequence, comprising: (a) a capture probe comprising a nucleic acid sequence capable of hydridizing to at least a portion of said amplified target nucleic acid sequence, said capture probe being immobilized on a solid phase support which forms a part of or is insertable into a container for the sample, and said capture probe being incapable of participating in standard nucleic acid sequence amplification processes, (b) reagents for amplification of said target nucleic acid sequence, and (c) means for detecting said target nucleic acid sequence, when bound by said capture probe.

23 Claims, 1 Drawing Sheet

M. FERMENTANS (INCOGNITUS) SNAAC TARGET

PRIMER 1

INSERTION-SEQUENCE-
LIKE ELEMENT

5'-GTTAGAAAACGTAGAAGAGAATGGCCACAGC-3'

1150 1160 1180 1200
5'-GAATGGTTGGTAAAATGTTAGAAAACGTAGAAGAGAATGGCCACAGCTTAAAAAATG
3'-CTTACCAACCACTTTACAATCTTTTGCATCTTCTCTTACCGGTGTCGAATTTTTTAC

SNAAC CAPTURE PROBE TATT-3'
5'-CATTCTGATCAAGGATGAC
NON-HYBRIDISING 3'-END 1220 1240 1260
TATTATTACATTCTGATCAAGGATGACAATACACTCATCAAGATTATATTGATTATT
ATAATAATGTAAGACTAGTTCCTACTGTTATGTGAGTAGTTCTAATATAACTAATAA 1280 1300 1310
TGAAAGAAAAACAAACAACTCAAAGCATGTCAAGAAAGGGAAATTGTTTAGACAA-3'
ACTTTCTTTTTGTTTGTTGAGTTTCGTACAGTTCTTTCCCTTTAACAAATCTGTT-5'

3'-GTTTGTTGAGTTTCGTACAGTTCTTTCCC-BIOTIN-5'
BIOTINYL-PRIMER 2

FIGURE 1

AMPLIFICATION AND DETECTION PROCESS

BACKGROUND OF THE INVENTION

Hybridisation methods are widely utilised in testing for the presence of particular nucleic acid sequences, identifying and/or quantifying such sequences.

Various improvements and modifications have been introduced, to improve the specificity and sensitivity of the reaction. For example, a number of recently developed in vitro nucleic acid amplification methods have greatly increased the sensitivity of detection. These methods include: ligase chain reaction (LCR), nucleic acid sequence based amplification (NASBA), $Q_\beta$ replicase based methods, strand displacement amplification (SDA) and notably polymerase chain reaction (PCR).

In a recent development, two separate PCR amplifications have been used to both amplify and label the target nucleic acid sequence. The labelled sequence is then immobilised on a solid phase carrier, and testing is carried out using a reagent specific to the label. (See D J Kemp et al, "Colorimetric detection of specific DNA segments amplified by polymerase chain reactions", *Proc Natl Acad Sci USA* 86, pp 2423–2427, 1989.)

However, in prior art methods, including that of Kemp et al, solution amplified nucleic acids have been detected in a second vessel by capture of hybridisation to solid phase capture reagents (two vessel assays).

Solid phase techniques have been used in relation to synthesis procedures (e.g. chemical synthesis of amino acid and nucleic acid sequences) and assay procedures (as in the final step of the procedure of Kemp et al, see above).

However, it has not hitherto been possible to conduct an in solution amplification process for nucleic acid sequences, and identification/quantification procedures, in the same reaction vessel.

SUMMARY OF THE INVENTION

This method for detecting a target nucleic acid sequence involves amplification and detection in the same vessel and comprises:

(a) amplification of the target nucleic sequence in a vessel which is provided with a solid phase capture probe comprising a nucleic acid sequence capable of hybridising to at least a portion of said amplified target nucleic acid sequence, said capture probe being incapable of participating or not participating in standard nucleic acid sequence amplification processes, (b) bringing a sample suspected of comprising said target nucleic acid sequence into contact with said capture probe under conditions which allow said amplified target nucleic acid sequence to be bound by said capture probe, and (c) detecting the presence of bound target nucleic acid sequence.

In a further aspect, the present invention provides an assay system or kit, for detecting a target nucleic acid sequence in a sample suspected of comprising said target nucleic acid sequence, comprising:

(a) a capture probe comprising a nucleic acid sequence capable of hybridising to at least a portion of said amplified target nucleic acid sequence, said capture probe being immobilised on a solid phase support which forms a part of or is insertable into a container for the sample, and said capture probe being incapable of participating in standard nucleic acid sequence amplification processes, (b) reagents for amplification of said target nucleic acid sequence, and (c) means for detecting said target nucleic acid sequence, when bound by said capture probe.

A sample suspected of comprising a particular nucleic acid sequence is placed within a reaction vessel. If said particular nucleic acid sequence is present within the sample, then it is amplified freely in solution, by any means, to give a nucleic acid product (or derivative or analogue) carrying a detector tag and captured by a complementary solid phase capture probe present in the reaction vessel. The complementary solid phase capture probe is a nucleic acid sequence (or derivative or analogue) which is incapable of participating in amplification of said particular nucleic acid sequence (e.g. will not act as a primer). Preferably, the capture probe hybridises to a central section of the amplified nucleic acid sequence—away from any primer or primer complementary nucleic acid sequences. Thus, false positives arising from amplified primer-multimers (e.g. primer-dimers) are avoided. The captured nucleic acid sequence (or derivative or analogue) is then identified via the detector tag and/or quantified by conventional means (e.g. by fluorescence, for products carrying a fluorescent tag).

Preferably, said particular nucleic acid sequence is amplified prior to capture by the solid phase capture probe. As the solid phase capture probe is incapable of participating in the amplification process, both amplification and capture can take place in the same reaction vessel. This represents a major advance over prior art systems. The system offers rapid detection with few manipulations and reduced risk of contamination of laboratories with amplicons (amplification products) compared to two vessel assays. The system thus facilitates processing of large numbers of diagnostic assays. Preparation of target nucleic acid sequences from specimens in the same reaction vessel is also possible.

Identification and quantification are preferably by means of a tag introduced during amplification.

For example, the process may be as follows: Nucleic acid sequences (or derivatives or analogues), amplified by any means in solution and carrying an introduced tag to enable detection, are captured during or after the amplification process by a complementary solid phase capture probe (as described above) present in the amplification reaction vessel. The captured nucleic acid sequence (or derivative or analogue) is then identified and quantified by means of the introduced detector tag.

Although it is preferable for amplification, capture, detection and quantification to occur in the same reaction vessel, it is also possible for detection and quantification to take place in a second reaction vessel. In the first reaction vessel, the nucleic acid sequence is amplified and tagged in solution, and the product is captured on a solid phase added prior to commencement of amplification (e.g. dipstick or beads—paramagnetic or non-magnetic) carrying a capture probe, incapable of participating in the amplification process. The dipstick, or suchlike solid phase, is then transferred to a second reaction vessel, where detection and quantification of the captured product takes place. This may prove advantageous in specific circumstances, e.g. calorimetric detection of specific nucleic acid sequences by isothermal amplification, capture of tagged (e.g. biotinylated) products via dipstick-solid phase probe in the first vessel and, in a second vessel, visual calorimetric detection via avidin-horseradish peroxidase.

DETAILED DESCRIPTION OF THE INVENTION

The present invention will now be described in more detail, and with respect to specific embodiments. It should be noted that these specific embodiments are presented as illustrative, but not restrictive, of the present invention.

The various stages of the SEQUENTIAL NUCLEIC ACID AMPLIFICATION AND CAPTURE (SNAAC) PROCESS are as follows:

1. Provision of Solid Phase Capture Probe

The reaction vessel comprises a solid phase capture probe which is incapable of participation in nucleic acid amplification. For example, the capture probe is covalently linked to the inside surface or wall of the reaction vessel via its 3'-end, or the 3'-end is modified such that it cannot participate in polymerase mediated amplification. The 5'-end lacks a phosphate and, therefore, the capture probe cannot participate in LCR (ligase chain reaction).

Instead of being attached to the wall of the reaction vessel, the capture probe can be attached to solid phase material (e.g. paramagnetic or non-magnetic beads, dipstick etc.) which is immersible into the reaction vessel. Such solid phase material is added prior to commencement of amplification.

2. Nucleic Acid Sequence Amplification and Tagging

A sample, either comprising or suspected of comprising the target nucleic acid sequence, is added to the reaction vessel. The target nucleic acid sequence may comprise either DNA or RNA.

Any amplification process, e.g. PCR, LCR, NASBA, $Q_\beta$ replicase based amplification, SDA or other amplification process, is carried out, to both amplify the nucleic acid sequence and introduce a detector tag into the amplified product. The detector tag is, for example, a biotin group (labelled as b in the diagram above), which is introduced via a biotinylated primer oligodeoxynucleotide sequence or analogue capable of being incorporated into the nucleic acid product during amplification (e.g. biotin dUTP). Other tags, such as fluorophores or europium chelates, can also be used. The product is a single or double stranded amplified nucleic acid product carrying a tag (e.g. biotin or a fluorophore).

3. Denaturation of Amplified Product

At completion of amplification, the tagged double stranded nucleic acid sequence (or derivative or analogue) is denatured (e.g. by heat) to give a single stranded form. This step is omitted for amplified (or non amplified) tagged single stranded nucleic acid sequences (or derivatives or analogues), such as produced by asymmetric in vitro amplification processes.

In the diagram above, (−) signifies the tagged product strand comprising a sequence complementary to the sequence of the capture probe, signified as (+).

4. Solid Phase Capture of Tagged Amplified Product

The reaction mixture is cooled, preferably to optimal annealing temperature, thus resulting in the tagged amplified nucleic acid sequence being captured by the capture probe (via standard AT and GC pairings, and including non standard pairings). Non-captured materials are then washed out of the reaction vessel.

Preferably, the capture probe hybridises to a central section of the amplified nucleic acid sequence—away from any primer or primer complementary nucleic acid sequences. Thus, primer dimers—often formed during PCR—do not give false positives. For LCR, capture occurs across the ligase joined oligodeoxynucleotides.

The capture probe may need to be approximately 15 nucleotides in length, to avoid hindering solution phase nucleic acid amplification. It should be noted, however, that optimal capture probe length remains to be determined. Indeed, it is probable that long capture probes may be useful, as they are unlikely to significantly interfere in amplification because of their solid phase character.

Nucleic acid amplification processes which give an excess of one of the product strands are preferred. This minimises competition between the capture probe, designated (+), and the (+) strand of the amplified product for hybridisation to the target (−) amplified product strand. Possible amplification processes include asymmetric versions of PCR and asymmetric LCR, NASBA and SDA—$Q_{62}$ replicase based methods give predominantly single-stranded product.

5. Product Identification and Quantification

Various standard methods can be used to identify and quantify the biotinylated captured product.

For example, the biotinylated captured product can be reacted with Europium labelled avidin or streptavidin, and time resolved fluorescence methods can then be used to identify and quantify the amount of Europium (see the diagram above).

Alternatively, the biotinylated captured product can be reacted with avidin-horseradish peroxidase, and spectrophotometric methods can then be used to identify and quantify the coloured product produced on addition of peroxidase substrate.

Other detection methods can also be used, e.g. fluorescence where b is a fluorescent tag, instead of biotin, and especially tags consisting of heat stable europium chelates with the amplification primer (Dahlen et al, 1991, *Molecular and Cellular Probes*, 5, 143).

Various aspects of the SNAAC process will now be described in more detail, with reference to particular embodiments:

Capture Probe Specifications

The capture probe is a totally or partially single-stranded nucleic acid sequence (or derivative or analogue) which is present in the reaction vessel, either attached to the reaction vessel surface or to added material (e.g. paramagnetic or non-paramagnetic beads, dipsticks etc.). The capture probe is incapable of participation in the amplification stage. For example, it may be a capture oligodeoxynucleotide in which the 3'-end is chemically bonded to the wall of the reaction vessel or bonded to solid phase material added to the reaction vessel (e.g. paramagnetic or non-paramagnetic beads, dipsticks etc.), and being capable of capturing, via complementary pairing (of the standard AT and GC pairings, and including non-standard pairings), totally or partially single-stranded, amplified RNA or DNA sequences (or derivatives or analogues, or sequences which are non-amplified but labelled with a detector tag), which carry an introduced tag to enable detection. Double-stranded amplified nucleic acid sequences are denatured prior to capture. For LCR, both 5' and 3' ends of the capture probe are rendered non-ligatable. The 3' end is blocked as described above, while the 5' end of the capture probe is rendered incapable of ligation e.g. via lack of a 5'-phosphoryl group or presence of any of a wide variety of 5' substituents (such as 5'-amino link or 5'-thiol). Alternatively, linkage to the solid support through the 5' end would also serve the same purpose. The 3' end would also be blocked via the above methods.

In summary, the capture probe comprises: a product capture nucleic acid sequence, a 3'-terminus which is rendered unavailable for participation in any in vitro amplification process by the presence of a 3'-amplification blocking group, and a nucleic acid spacer arm between the capture sequence and the point of attachment to a solid phase linker which is, in turn, attached to a solid support (such as a reaction vessel surface).

1. Solid Supports

The solid support material can be, for example, polystyrene, polycarbonate, polypropylene, nylon or glass, but the support is not limited to these examples. The solid support may be the inside surface of the reaction vessel or material (e.g. paramagnetic or non-paramagnetic beads, dipsticks etc.) added prior to commencement of amplification. It may take the form of e.g.:

(a) Microtitre trays composed of any plastic (e.g. polystyrene or polycarbonate), including tube assemblies (such as the 96 tube array) of Perkin Elmer Cetus for the GeneAmp PCR System 9000, standard 96 well (8×12) microtitre trays, such as Covalink trays (Nunc) which carry methylamino groups, standard microtitre trays chemically modified by nitration and reduction (or other chemistries) to generate amino groups on the inside surfaces of the wells, and similar trays modified for temperature cycling (i.e. thin-walled and capable of being sealed).

(b) Individual test tubes suited for nucleic acid amplification, preferably with individual sealing enclosures, but also with other means of sealing (e.g. adhesive plastic strip). The test tubes may be part of a kit, and fit into regularly spaced apertures in an arrangement similar to a microtitre tray (e.g. 96 well, industry standards 8 ×12 form).

(c) Microtitre tray lids with protrusions which fit into microtitre trays, e.g. Fast Elisa dish—Falcon.

(d) Paramagnetic or non-paramagnetic beads, e.g. Affigel-Pharmacia. Also, Abbott bead system and paramagnetic beads, e.g. Dyna beads (Dynal, Oslo, Norway).

(e) Dipsticks—for rapid applications, e.g. suburban and country medical practices, and in diagnostic field work.

These all offer the potential for high volume diagnostic applications for Sequential Nucleic Acid Amplification and Capture (SNAAC), especially if isothermal (single temperature) amplification is used.

2. Solid Phase Linker

Linkage of the capture probe to a solid support can be via absorption or, preferably, via covalent bonding. The latter will withstand the high temperatures required by some nucleic acid amplification processes (e.g. the 94° C. step in PCR).

A wide variety of solid phase linkers can be used. These are formed by reaction of a solid support having any of a range of functionalities (see below) and reactive linking groups of the capture probe.

Examples of solid supports (SS) with functional groups for covalent attachment of capture probes are given below:

(a) SS—$SO_2$—NH—$(CH_2)_n$—$NH_2$
(n=0–8)

(b) SS—$NH_2$ (c) SS—NH—CO—$CH_2$—I(or Br)

(d) SS—CO$_2$—NHS
   (NHS=N-hydroxysuccinimide)
(e) SS—CHO
(f) SS—CH$_2$—O—tresyl
(g) SS—SH This list is exemplary only, and is not exhaustive (see S. Wong, "Chemistry of Protein Conjugation and Cross Linking", CRC Press, 1993.

Illustrative (non-exhaustive) examples of capture probes with chemical linking groups and methods for coupling to the above solid supports include:

(i) 5' or 3'-phosphoryl capture probe (or internal phosphoryl group) will link to (a) or (b) above in the presence of a water soluble carbodiimide (e.g. 1-ethyl-3-(3-dimethylaminopropyl)-carbodiimide, EDC).

(ii) 5' or 3' or internal thiol derivatised capture probe will directly link to (c) above.

(iii) 5' or 3' or internal amino derivatised capture probe will link to (d) or (e) or (f) (reduction is required following reaction with (e)).

(iv) 5' or 3' or internal carboxyl—NHS derivatised capture probe will linked to (a) or (b) above.

(v) 5' or 3' or internal amino iodoacetyl (or bromoacetyl) derivatised capture probe will link to (g) above.

These examples are not limiting.

3. Nucleic Acid Spacer Arm

This may be up to 150 nucleotides in length and be of any composition (including natural deoxy- or ribonucleotides or their phosphorothioate or methyl phosphonate derivatives). It may comprise, in part, a palindrome which forms a double-stranded "snap back" region containing a unique and perhaps rare restriction site (e.g. Not I or SfiI). The latter allows cleavage of any solid phase amplified and captured product for subsequent characterisations.

4. Probe Capture Sequence

This may be 12–150 nucleotides in length (optimally 12–18 nucleotides) and complementary to a section (amplified product target site) of one strand of the amplified nucleic acid product. The product target site is a sequence in the length range of 12–150 nucleotides (optimally 15–18 nucleotides), but not limited to these examples. The product target site is away from primer sequences and their complements. However, for methods where the amplified product is formed only from the primers (e.g. Ligase Chain Reaction, LCR), then the product target sequence will be in part of one strand of two joined primers and will span across the joining point. The capture probe and capture conditions will be such as to only allow capture of the amplified product (comprising the detector tag) and not allow capture of the original primer carrying the detector tag.

Probe 3'-Amplification Blocking Group

Oligodeoxynucleotide capture probes which cannot participate in nucleic acid amplification processes can be prepared in various ways, including (but not limited to) the methods described below.

For oligodeoxynucleotide capture probes, the 3'-end must not comprise a free 3'-hydroxyl group (or biologically equivalent group) as these may participate in polymerase based amplification processes. Similarly for LCR—preferably, the 5'-end should not contain a 5'-phosphate, as this may participate in ligation.

The 3'-end of the capture probe is modified to prevent it from participating in nucleic acid amplification. This can be accomplished in two general ways—the first giving rise to Type I capture probes, and the second giving rise to Type II capture probes.

Type I Capture Probes

These are linked to solid supports through the 3'-end. Such linked capture probes cannot participate in polymerase mediated amplification. One example of the preparation of a Type I probe is the linking, via a water-soluble carbodiimide, of a 3'-phosphoryl capture probe to a solid support carrying primary or secondary (e.g. —NH—-CH$_3$) amino groups.

Type II Capture Probes

These are probes which are linked to solid supports via the 5'-end of the probe. Currently available automated nucleic acid synthetic chemistries favour the 5'-modification of oligonucleotides. For example, 5'-amino linked and 5'-thiolated derivatives of oligonucleotides can be readily synthesised and subsequently linked to solid supports (see examples above). However, the free 3'-end of the capture probe should be prepared in a form which prevents its participation in nucleic acid amplification. Prevention of the participation of the capture probe in in vitro amplification by blocking the 3'-end of the probe is a crucial novel and useful feature of the Sequential Nucleic Acid Amplification and Capture (SNAAC) process. It allows the capture probe to be included in the same reaction tube as that in which the nucleic acids are amplified. The subsequent one tube amplification and product detection assay offers considerable saving of operator time and offers reduced contamination of the laboratory with amplicons.

Examples of 3'-blocking modifications are listed below:

(i) A short nucleic acid extension at the 3'-end to give a sequence which is non-complementary to the input target nucleic acid sequence (which is to be amplified by the SNAAC process).

CAPTURE OF BIOTINYLATED AMPLIFIED NUCLEIC ACID BY SNAAC PROBE

1. Solid Support

One strand of amplified nucleic acid product - captured by hybridisation to probe capture sequence

- Biotin - 5'

2. Solid phase linker

5. Probe 3' amplification blocking group, e.g. non - complementary nucleotide sequence extension prevents participation in amplification 3. Nucleic acid spacer arm 4. Probe capture sequence Other examples include:
  (ii) The presence of a 3'-phosphoryl group.
  (iii) The presence of a 3'-dideoxy terminator nucleotide, e.g. ddTMP or other dideoxy terminator (added by terminal transferase and ddTTP).

These examples are non-exhaustive. In fact, any 3'-chemical group, which is not accepted by DNA polymerases as a priming site for DNA synthesis, can be used.

Specific examples of capture probe preparation, which are illustrative but non-limiting of the invention, are described in more details below.

Preparation of Capture Probes with a 3'-end Substituent to Enable Coupling to Solid Phases Probes without an available 3'-hydroxyl, e.g. those linked via the 3'-end, cannot participate in polymerase-dependent DNA amplification.

Preparation of Capture Probes with a 3'-phosphoryl Group

DMT-ESE-O      O
         \\  //
          P          +   HO—X—(CPG)
         / \
 (iProp)$_2$N   O
              |
             CNEt dimethoxytrityl-ethyl-sulphonylethyl-
cyanoethyl-phosphoramidite Coupling in automated
DNA synthesizer O
        ||
DMT-ESE-O—P—X—(CPG)
        |
        O
        |
       CNEt In the above reaction scheme,
DMT=dimethoxytrityl ESE=ethyl-sulphonylethyl
iProp=isopropyl
CNEt=cyanoethyl
X=spacer arm
CPG=control pore glass (or other solid support).

The spacer arm X can be a variety of chemical substances, including any deoxynucleotide with free 5'-hydroxyl (e.g. thymidine) and linked via the 3'-hydroxyl to the CPG support.

After the above coupling reaction, the DMT (dimethoxytrityl) group is removed and synthesis continues by standard phosphoramidite chemistry (automated). For example, after the first addition of protected dinucleoside phosphoramidite, the following product is formed:

Y
              |
              B       O           O
              |       ||          ||
5'-DMT—O—D—O—P—O—ESE—O—P—O—X—(CPG)
                  |  3'          |
                  O              O
                  |              |
                 CNEt           CNEt

B=base (i.e. A,C,G or T)
D=deoxyribose
DMT=dimethoxytrityl
X=spacer arm
CNEt=cyanoethyl
ESE=ethyl-sulphonylethyl
Y=base protecting group
CPG=control pore glass (or other solid support).

Further deoxynucleoside phosphoramidites are added to complete the assembly of the protected 3'-phosphorylated capture probe.

The final protected oligodeoxynucleotide capture probe, linked to CPG, has the following form:

Final 3' phosphorytated capture reagent

DMT=dimethoxytrityl $B_1, B_2$ etc.=base (i.e. A,C,G or T)

D=deoxyribose

X=spacer arm p=phosphoryl

CNEt=cyanoethyl

ESE=ethyl-sulphonylethyl

Y=base protecting group

CPG=control pore glass (or other solid support).

N. B. Simpler chemistries for 3-phosphorylation are theoretically possible.

The capture probe is then covalently linked to the wall of the reaction vessel (or bead or dipstick), e.g. the probe is linked through the 3'-phosphoryl group via 1-ethyl-3-(3-dimethylaminopropyl)-carbodiimide (EDC) to polystyrene or polycarbonate (or other material) microtitre wells which are derivatised with primary or secondary (e.g. Covalink trays) amino groups.

Similarly, capture probes carrying a 3'-amino or a 3'-thiol group can be covalently linked to surfaces derivatised with carboxyl groups (N-hydroxysuccinimide activated) or bromoacetic acid respectively.

5'-End linked 3'-end blocked capture probes can be prepared as follows:

| 5'-Phosphoryl group enables linkage to solid supports, e.g. linkage via EDC to solid supports with covalently attached amino groups. | Dideoxynucleotide (introduced via terminal transferase and a dideoxynucleotide triphosphate) caps 3'-end of capture probe, lacks 3'-hydroxyl group and prevents participation of capture probe in polymerase-mediated nucleic acid amplification processes. Other 3'-terminal modifications which prevent involvement in amplification are also possible (see later). |

$B_1$, $B_2$ etc.=base (i.e. A,C,G or T)
D=deoxyribose
p=phosphoryl
dD=dideoxyribose.

Similarly, 5'-amino group or 5'-thiol group terminated probes can be covalently linked to solid supports which have covalently attached carboxyl groups (N-hydroxysuccinimide activated) or bromoacetyl groups respectively.

There are other 3'-substituents which render the solid phase capture probe incapable of participating as a primer in amplification of target nucleic acid sequences (see list below).

General Formula

For example, R can be any of the following (list not exhaustive):

(a) R=3'-oligodeoxynucleotide extension which is not complementary to the target, i.e. does not act as a primer for nucleic acid synthesis (e.g. for PCR) or does not act as a ligase substrate (e.g. for LCR).

(b) R=3'-amino link.
(c) R=3'-phosphoryl group.
(d) R=3'-biotin.
(e) Other modifications are also possible.

Other capture probe variants are possible, e.g. phosphorothioate capture probes:

$B_1$, $B_2$ etc.=base (i.e. A,C,G or T)
D=deoxyribose
p=phosphoryl
p=phosphorothioate group
s
R1=5'-hydroxyl group and R2=3'-phosphoryl group, for example.

The phosphorothioate capture probe variants may offer advantages, e.g. resistance to degradation during workup of the specimen to extract the target nucleic acid sequence in the reaction vessel, prior to nucleic acid amplification.

Nucleic Acid Amplification

The SNAAC process of the present invention is applicable to any method of nucleic acid amplification. Examples of types of in vitro Nucleic Acid Amplification processes, in which SNAAC may be utilised, are as follows:

(a) PCR (Polymerase Chain Reaction)
(b) LCR (Ligase Chain Reaction)
(c) NASBA (Nucleic Acid Sequence Based Amplification), using RT/RNAase H/$T_7$ polymerase (wherein RT=reverse transcriptase, RNAase H=ribonuclease H, $t_7$ polymerase=$T_7$ bacteriophage RNA polymerase).
(d) QBRDA (Qβ Replicase Dependent Amplification).
(e) SDA (Strand Displacement Amplification).

SNAAC is applicable to both standard amplification processes of PCR, LCR, NASBA, QBRDA and SDA and modifications—particularly those which produce a preponderance of one amplified product nucleic acid strand (i.e. asymmetric amplification versions). The preponderant strand produced must be that which is complementary to the capture probe. (N.B. QBRDA produces a single-stranded RNA product.) SNAAC is applicable to PCR, for example, in the form of standard PCR (to give a double-stranded DNA product), nested PCR (3 or 4 primers) and asymmetric PCR versions (which give a preponderance of one amplified strand, complementary to the capture probe).

The principles of PCR, LCR, NASBA QBRDA and SDA amplification methods are described below:

PCR (Polymerase Chain Reaction)
See R K Saiki et al, "Enzymatic amplification of β-globin genomic sequences and restriction site analysis for diagnosis of sickle cell anaemia", *Science* 230, pp 1350–1354, 1985.

(b) LCR (Ligase Chain Reaction)
See F Barany, "Genetic disease detection and DNA amplification using cloned thermostable ligase", *Proc Natl Acad Sci USA* 88, pp 189–193, 1991.

(c) NASBA (Nucleic Acid Sequence Based Amplification)

See J Guatelli et al, "Isothermal in vitro amplification of nucleic acids by a multienzyme reaction modelled after retroviral replication", *Proc Natl Acad Sci USA* 87, pp 1874–1878, 1990.

Strategy of NASBA scheme. The reaction depends on a continuous cycle of reverse transcription and transcription reactions to replicate an RNA target by means of cDNA intermediates. DNA targets can also be amplified. Primers 1 and 2 prime DNA synthesis and Primer 1 encodes the promoter sequence for the T7 RNA polymerase (black boxes). Steps 1–6 depict the synthesis of a double-stranded cDNA, which is a transcription template for T7 RNA polymerase. Complete cDNA synthesis is dependent on the digestion of the RNA in the intermediate RNA.DNA hybrid (step 4) by RNase H. Transcription-competent cDNAs yield antisense RNA copies of the original target (step 7). These transcripts are converted to cDNAs containing double-stranded promoter on one end (steps 7–12).

These cDNAs yield antisense RNAs, which can re-enter the cycle. Thin lines, RNA; thick lines, DNA; RT, reverse transcription.

(d) Qβ Replicase Dependent Amplification

See P M Lizardi et al, "Exponential amplification of recombinant—RNA hybridization probes", *Bio/Technology* 6, pp 1197–1202, 1988, F R Kramer and P M Lizardi, "Replicatable RNA reporters", *Nature* 339, pp 401–402, 1989, and P M Lizardi and F R Kramer, "Exponential amplification of nucleic acids: new diagnostics using DNA polymerases and RNA replicases", *TIBTECH* (Elsevier Science Publishers Ltd., UK) 9, pp 53–58 (1991).

Qβ replicase-replicable RNA reporter based methods rely on either target dependent synthesis of replicatable RNA reporters, using three PCR cycles and T7 polymerase, or on repetitive cycles of target dependent sandwich capture and release of replicatable RNA reporters from paramagnetic particles. The replicatable RNA reporter produced by either of these methods is amplified as follows:

A replicase molecule (stippled) binds to a single-stranded RNA, and a complementary single-stranded RNA molecule is generated by copying and release. The parent and daughter strands both participate in new cycles of binding, copying and release. Therefore, amplification is exponential—in the presence of excess replicase, the number of strands doubles with each cycle of synthesis. Up to $10^8$ fold amplification of the replicatable reporter occurs in 30 minutes.

(e) SDA (Strand Displacement Amplification)

See G T Walker et al, "Strand displacement amplification—an isothermal, in vitro DNA amplification technique", *Nuc. Acid Res.* 20, pp 1691–1696, 1992.

Target generation scheme for SDA. This figure depicts the initial steps in an SDA reaction which transform the original target sequence into the amplification cycle depicted. A target DNA sample is heat denatured. Four primers ($B_1$, $B_2$, $S_1$, and $S_2$) present in excess, bind the target strands at positions flanking the sequence to be amplified. Primers $S_1$ and $S_2$ have HincII recognition sequences (5' GTTGAC) located 5' to the target complementary sequences. The four primers are simultaneously extended by exo$^-$ klenow using dGTP, dCTP, TTP and DATPS. Extension of B displaces the $S_1$ primer extension product, $S_1$-ext. Likewise, extension of $B_2$ displaces $S_2$-ext. $B_2$ and $S_2$ bind to displaced $S_1$-ext $B_1$ and $S_1$ bind to displaced $S_2$-ext. Extension and displacement reactions on templates $S_1$-ext and $S_2$-ext produce two fragments with a hemiphosphorothioate HincII at each end and two longer fragments with a hemiphosphorothioate HincII site at just one end. HincII nicking and exo$^-$ klenow extension/displacement reactions initiate at these four fragments, automatically entering the SDA reaction cycle depicted. Sense and antisense DNA strands are differentiated by thin and thick lines. HincII recognition sequences are depicted by (━).

The SDA reaction cycle. These reaction steps continuously cycle during the course of amplification. Present in excess are two SDA primers ($S_1$ and $S_2$). The 3'-end of $S_1$ binds to the 3'-end of the displaced target strand $T_1$, forming a duplex with 5'-overhangs. Likewise, $S_2$ binds $T_2$. The 5'-overhangs of $S_1$ and $S_2$ contain the Hinc II recognition sequence ($^{5'}$GTTGAC). Exo$^-$ klenow extends the 3'-ends of the duplexes using dGTP, dCTP, TTP and dATPS, which produces hemiphosphorothioate recognition sites on $S_1 \cdot T_1$ and $S_2 \cdot T_2$. HincII nicks the unmodified primer strands of the hemiphosphorothioate recognition sites, leaving intact the modified complementary strands. Exo$^{14}$klenow extends the 3'-end at the nick on $S_1 \cdot T_1$ and displaces the downstream strand that is equivalent to $T_2$. Likewise, extension at the nick on $S_2 \cdot T_2$ results in displacement of $T_1$. Nicking and polymerization/displacement steps cycle continuously on $S_1 \cdot T_1$ and $S_2 \cdot T_2$ because extension at a nick regenerates a nickable HincII recognition site. Target amplification is exponential because strands displaced from $S_1 \cdot T_1$ serve as target for $S_2$ while strands displaced from $S_2 \cdot T_2$ serve as target for $S_1$. Sense and antisense DNA strands are differentiated by thin and thick lines. Intact and nicked HincII recognition sequences are depicted by ▬ and ▬ ▬, respectively. The partial HincII recognition sequence $^{5'}$GAC and its complement $^{5'}$GTC are present at the 5'- and 3'-ends of displaced strands as represented by ▬ and ▬.

| | One Primer incorporated | Two or more primers incorporated | Double stranded product | Excess single stranded product possible | Can be labelled at non-anchored end | Can be internally labelled | Requires temperature cycling |
|---|---|---|---|---|---|---|---|
| CHARACTERISTICS OF VARIOUS NUCLEIC ACID AMPLIFICATION SYSTEMS | | | | | | | |
| 1. PCR | + | + | + | + | + | + | + |
| 2. LCR (Ligase chain reaction) | + | + | + | + | + | Probably | + |
| 3. NASBA* RT/T7 | + | + | + | + | + | + | No 42° C. only** |
| 4. Qβ | + −*** | + −*** | No | + | + −*** | + | No** |
| 5. SDA | + | + | + | + | + | + | No** |

*NASBA = Nucleic acid sequence based amplification
**Isothermal amplification offers an appreciable technical advantage over thermal cycling
***Several versions of QB replicase based amplification are known - one utilises PCR primers and the other does not use primers
Detection systems for Solid Phase Amplified Nucleic Acid Sequences
Any suitable method for labelling nucleic acid sequences can be used, e.g. fluorescent labelling, biotin labelling or enzyme labelling. The label is introduced into the amplified nucleic acid product either via labelled primers or via labelled nucleotide substrates.

Nucleic Acid Composition of the Capture Probe

The type of nucleotides comprising the capture probe can include any which are capable of specifically hybridising to an amplified nucleic acid product. These include:

(i) Standard DNA nucleotides or their phosphorothioate or methyl phosphonate derivatives. The latter two classes of derivatives may be preferred due to the resistance to nucleuses of nucleic acid sequences composed of these derivatives.

(ii) Standard RNA nucleotides or their phosphorothioate or methyl phosphonate derivatives.

(iii) For positions where the product target sequence may vary, the capture probe may comprise a non-standard chemical entity which will hybridise to all possible target sequences, e.g. one or more IMP or dIMP (or phosphorothiocate or methyl phosphonate derivative residues) may be included in the capture section of the capture probe. Alternatively, several probes of different sequences (or comprising mixed sequences) can be used in a single SNAAC assay.

Discrimination by Capture Probe

Where normal and/or mutant sequences are amplified, the capture probe can be designed and used to discriminate (via hybridisation or not) between two or more different sequences. For example, capture probe N in one SNAAC assay will only capture the normal amplified sequence, while capture probe M in another SNAAC assay will only capture the mutant amplified sequence. Alternatively, where two or more amplified products of different sequence are formed, the capture probe is modified to comprise chemical entities which will bind to and capture either or any of the possible amplified sequences produced. Examples of such capture probes include these comprising one or more residues of IMP or dIMP (or phosphorothiate or methyl phosphonate derivatives). Inosine forms complementary pairs with A, C, G or T. Alternatively, multiple probes can be prepared and used collectively (i.e. in one assay) in solid phase form for the capture of any of the possible amplified product nucleic acid sequences.

AMPLIFIED NUCLEIC ACID LABELS

Exemplary detection systems include fluorescent labels, time resolved fluorescent labels, biotin, avidin, streptavidin, radiolables, enzymes, dyes, intercalators and rare earth metals, for example:

(a) Fluorescent labelling and detection
  Source of fluorescent label
    (i) Fluorescent primer, e.g. fluorescein-primer.
    (ii) Fluorescent derivatives of ribo- or deoxyribo-NTP's (substrates for RNA and DNA polymerases, respectively).
  SNAAC Product: Fluorescently labelled nucleic acid, captured by a solid phase capture probe.
  Detection System: Fluorescent plate reader or other fluorescence detection system.

(b) Biotin labelling and detection
  Source of biotin label
    (i) Biotinylated primer.
    (ii) Biotinylated dNTP's, e.g. biotinylated DATP.
  SNAAC Product: Biotin labelled nucleic acid, captured by a solid phase capture probe.
  Detection Systems
    (i) Europium labelled avidin/streptavidin, with quantification of Europium by time resolved fluorescence spectroscopy.
    (ii) Avidin/streptavidin—horseradish peroxidase, with quantification of the resulting coloured product by spectroscopy (e.g. plate reader).
    (iii) Avidin/streptavidin—alkaline phosphatase, with quantification of the resulting coloured or fluorescent product by standard or fluorescent spectroscopy.

(c) Other labelling and detection systems, e.g. rare earth metals

Nucleic acid labels include rare earth labelled primers which can survive the elevated temperatures required in some of the nucleic acid amplification processes (e.g. 94° C. in PCR).

Applications

The methods of the present method can be used in any situation where it is necessary to test for the presence of particular nucleic acid sequences, identify and/or quantify such sequences. Accordingly, the possible applications are many and varied.

The following are a few examples of such applications:

1. Pathogen Detection.
    Detection of viruses (HIV, hepatitis viruses, papilloma).
    Detection of microorganisms (Mycobacteria, Legionella, Mycoplasmas).
    (Applications in clinical medicine, veterinary science, aquaculture, horticulture and agriculture.)

2. (a) Detection of sequence variations which cause or are associated with a disease or are genetically linked to a disease locus. Examples cover genetic diseases and cancer.
    e.g. Point mutations—Sickle cell anaemia, phenylketonuria, Lesch Nyhan syndrome.
    Small deletions—Cystic Fibrosis (F508).
    Large deletions—β-thalassaemia, Duchenne muscular dystrophy.
    Sequence reiteration—Fragile X.
    RFLP's—Huntington's chorea,
    (Restriction Fragment Length Polymorphisms) β-thalassaemia, cystic fibrosis.
  (b) Population screening for carriers of serious genetic diseases, where the incidence of carriers is high and the number of mutations is low, e.g. cystic fibrosis, and Tay Sach's disease in Ashkenazi Jews.

3. Cancer—detection of predisposing sequences, e.g. philadelphia chromosomes in chronic myelogenous leukaemia, antibody gene rearrangements, specific deletions, point mutations; detection and monitoring of treatment, remission and relapse.

4. Tissue typing—determination of HLA genotypes.

5. Forensic applications—e.g. VNTR DNA fingerprinting of individuals and obtaining DNA fingerprints from forensic samples.

6. Maternity and paternity testing.

7. Foetal sex determination.

8. Taxonomy.
    Classification and speciation of organisms (prokaryotes and eukaryotes). At present, speciation of higher organisms is largely based on morphological features and thus speciation is extremely difficult—SNAAC has great potential here.

9. Quality control in agriculture and the food and pharmaceutical industries, e.g. assessment of authenticity of food products.

Advantages of Snaac Over Previously Known Nucleic Acid Amplification Processes (a) SNAAC allows single tube nucleic acid amplification, amplified product capture and detection, and product quantification. (Probably, target nucleic acid sequence preparation can also be carried out in the same tube, particularly if phosphorothioate or methyl phosphonate forms of the capture probe are used.)

(b) Reduction of false positives due to primer-dimer formation. Primer-dimers have the potential to cause problems with other solid phase nucleic acid sequence amplification methods. In such methods, a false positive result will be obtained if a solid phase primer-dimer carrying the detector tag is produced. However, with SNAAC, primer-dimers will not be captured, as they lack the amplified target site—thus, they will not be captured and a signal will not be obtained.

(c) SNAAC allows significant reduction in the spread of amplicons and the probability of subsequent contamination of other amplification assays to give false positives. With SNAAC, there is no need to transfer or pipette amplicons to other locations for detection and quantification. The following widely used product detection and quantification techniques, which pose considerable risk with respect to the probability of amplicon spread, are avoided—agarose gel electrophoresis; dot blot hybridisation in a second assay tube or on a membrane. The amplicons in the final SNAAC washes (carried out just prior to captured product detection) can be readily inactivated by deposition in acid, e.g. 1M HCL (1 hour).

This invention may be embodied in other forms or carried out in other ways without departing from the essential principles thereof. The present disclosure is therefore to be considered, in all respects, as illustrative and not restrictive of the invention, the scope of which is indicated by the appended claims.

The following examples provide details of specific materials and techniques. However, they are exemplary only, and are not restrictive of the present invention.

EXAMPLE 1

SNAAC was applied to the detection of *Mycoplasma fermentans* strain incognitus—a mycoplasma frequently found in male homosexuals and AIDS-positive individuals. The amplification technique used was asymmetric PCR and the target was a 138 base pair section of an insertion-sequence-like element (see FIG. 1), (Hu et al, 1990, *Gene*, 93, p. 67). The PCR primers and capture probe (see FIG. 1 for sequences) were synthesised by an applied biosystems PCR-MATE DNA synthesiser.

Derivatisation of Microtitre Plates with SNAAC Capture Probe

Thin-walled polycarbonate plates (HYTR3MT, Integrated Sciences, Sydney, Australia), with the supporting side flanges cut of, were covalently derivatised with the oligodeoxynucleotide SNAAC capture probe.

Beneze moieties of the polycarbonate well surfaces were nitrated with acetyl nitrate and then reduced with either stannous chloride or sodium dithionite to give aminated surfaces. The SNAAC capture probe 5'-CATTCTGATCAAGGATGACTATT-3' (Sequence ID No. 3)comprised a 19 nucleotide section complementary to a portion of the biotinylated single-stranded DNA produced by asymmetric PCR in the aqueous phase of SNAAC assays, and a 3'-tetranucleotide tail which was not complementary to the PCR product, and which prevents participation of the oligonucleotide in PCR (this was confirmed by standard PCR, and the lack of a product as determined by agarose gel electrophoresis).

The capture probe was covalently coupled to the aminated surface of wells, using the water-soluble carbodiimide, 1-ethyl-3-(3-dimethylamino propyl)-carbodiimide (EDC). The wells were then extensively washed and used for SNAAC.

Asymmetric PCR Conditions

Each SNAAC (PCR) reaction mixture consisted of 10 mM Tris-HCl pH 8.3 (at 25° C.); 50 mM KCl; 0.04% gelatin; 2.0 mM $MgCl_2$; 200M dNTP's (Promega); 4 nM PCR primer 1, 5'-GTTAGAAAACGTAGAAGAGAATGGCCACAGC-3' (Sequence ID No. 1); 400 nM primer 2, %'-biotinyl-CCCTTTCTTGACATGCTTTGAGTTGTTTG-3' (Sequence ID No. 4)(Bresatec, Adelaide, Australia); target DNA, amounting to that from 5,000 organisms; and 2 units of AmpliTaq (Perkin Elmer). Oil was added, an adhesive seal cover was placed over the plate, and cycling, using the conditions given below, was carried out in a GeneAmp PCR System 9600 (Perkin Elmer Cetus).

| Initial target denaturation | 94° C. | 7 min |
|---|---|---|
| Primer annealing | 55° C. | 1 min |
| Elongation | 72° C. | 1 min 45 cycles |
| Amplicon denaturation | 94° C. | 1 min |
| Final capture of single stranded biotinylated amplified product | slow cooling from 72° C. to 20° C. | 10 min |

At completion of SNAAC, the liquid phase was, in some cases, collected and examined (by 2% agarose gel electrophoresis) for PCR amplified single-stranded biotinylated DNA product. This was found in plus target DNA *M. fermentans* SNAAC assays, but not in minus target DNA control assays (results not shown).

Detection of Captured *M. fermentans* Amplified Biotinylated Single-stranded DNA The oil was removed and the wells washed 6× with wash solution (0.05% v/v Tween 20, 50 mM NaCl, 6 mM $Na_2HPO_4$, 4 mM $NaH_2PO_4$, pH 7.3). The wells were blocked with skim milk, washed, and the captured biotinylated PCR product detected using europium-labelled streptavidin according to the manufacturer's instructions (Wallac, Oy, Turku, Finland). Eu-streptavidin (40 ng/well) in Delfia assay solution was allowed to bind briefly to the captured biotinylated DNA product, washed, then the bound europium was quantified by time resolved fluorescence in an ARCUS 1230 fluorometer (LKB-Wallac, Turku, Finland). Results are shown in Table 1.

TABLE 1

SNAAC DETECTION OF *MYCOPLASMA FERMENTANS*

SNAAC CONDITIONS

| + *M. fermentans* target DNA[A] | No target DNA | Assay Discrimination factor |
|---|---|---|
|  |  | +DNA counts / −DNA counts |
| Run 1 |  |  |
| 182,000 counts[b] | 5500 counts | 36 |
| Run 2 |  |  |
| 189,000 counts[b] | 5950 counts | 32 |

[a]from DNA equivalent to 5,000 organisms.
[b]background of 1800 counts subtracted from all values.
All assays carried out in quadruplicate.

TABLE 2

SPEFICITY OF *MYCOPLASMA FERMENTANS* SNAAC ASSAY

| Organism tested (Purified DNA)[a] | Europium counts[b] |
|---|---|
| *M. fermentans* | 90 000 |
| *M. gentialium* | 4 500 |
| *M. pneumoniae* | 3 800 |
| *M. hominis* | 2 200 |
| *A. laidlawii* A. | 4 300 |
| *E. coli* | 3 900 |

TABLE 2-continued

SPEFICITY OF MYCOPLASMA FERMENTANS SNAAC ASSAY

| Organism tested (Purified DNA)[a] | Europium counts[b] |
|---|---|
| Human | 4 200 |
| NoDNA | 3 200 |

[a]Mycoplasma DNA equivalent to approximately $10^6$ colony-forming units; E. coli and human DNA were tested at 0.5 g of DNA.
[b]Background, 800 counts subtracted. All values are the average of quadruplicate measurements.

The specificity of the *M. fermentans* SNAAC assay is excellent. Only *M. fermentans* DNA gave a signal greater than the arbitrary cut-off of 10 000 europium counts.

TABLE 3

SENSITIVITY OF MYCOPLASMA FERMENTANS SNAAC ASSAY WITH A CLONED TARGET

| M. fermentans cloned target number[a] | Europium counts[b] |
|---|---|
| $10^5$ | 144000 |
| $10^4$ | 37500 |
| $10^3$ | 49300 |
| $10^2$ | 4330 |
| 0 | 6170 |

Figure 1:
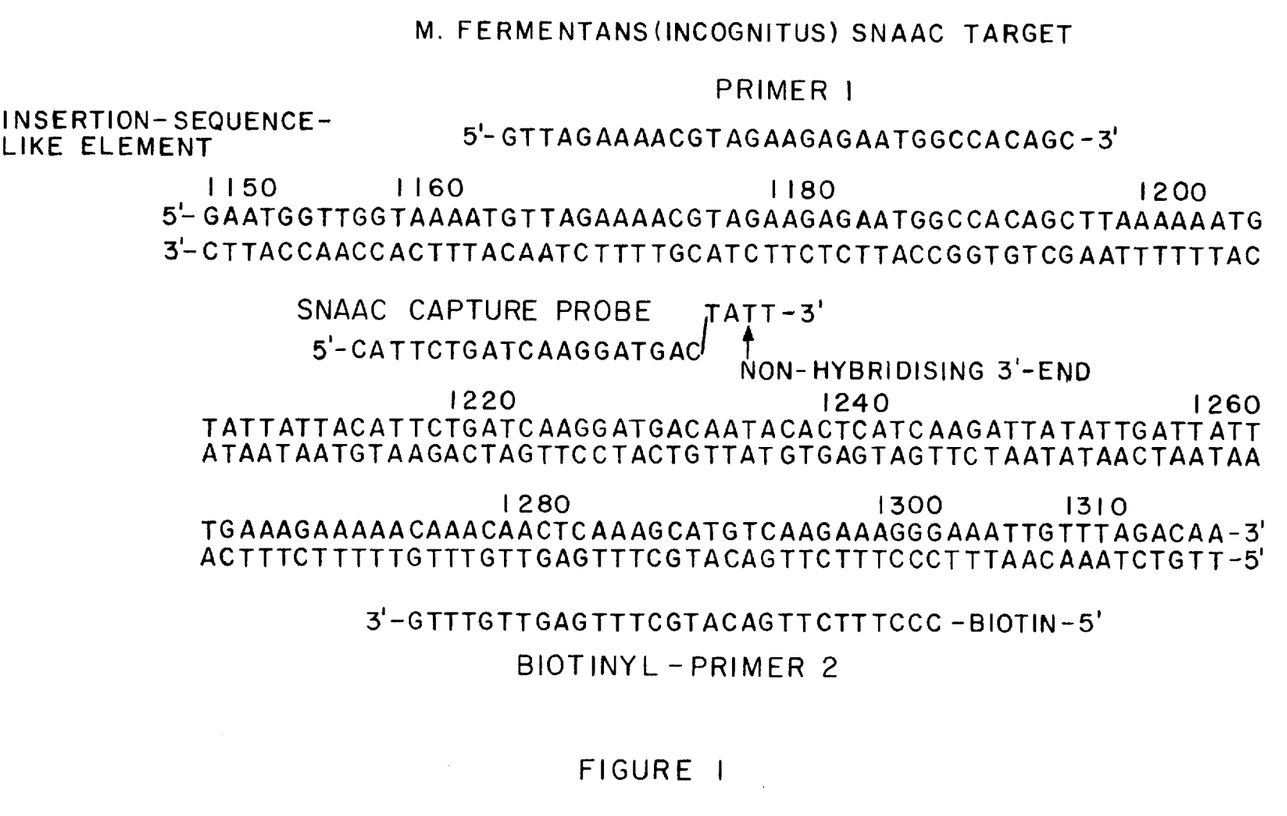
FIG. 1 shows the Primer 1, SNAAC Capture Probe and Biotinyl-Primer 2 sequences aligned with the corresponding areas of the insertion-sequence-like element sequence.

[a]The clone consisted of a 138 bp section of the insertion sequence like element of *M. fermentans* which was amplified with the primers depicted in FIG. 1; restricted with PstI and XbaI; cloned in pUC 18 and purified.
[b]Background 800 counts substracted. All points are averages of quadruplicate values.

The *Mycoplasma fermentans* SNAAC assay had a limit of detection of 1000 organisms. We expect this to be reduced after further optimisation of the process.

TABLE 4

SENSITIVITY OF M. FERMENTANS SNAAC ASSAY WITH CULTURED ORGANISMS

| M. fermentans concentration[a] cfu/assay | Europium counts[b] |
|---|---|
| $10^5$ | 165,000 |
| $10^4$ | 95,100 |
| $10^3$ | 36,500 |
| $10^2$ | 9,590 |
| 0 | 6,070 |

[a]the target was purified DNA which corresponded to the number of colony forming units of *M. fermentans* shown.
[b]background 820 counts, subtracted.

The *M. fermentans* SNAAC assay had a sensitivity limit between 100 and 1000 target (cloned) copies.

References throughout the specification and claims to nucleic acids or nucleic acid sequences should be taken, where appropriate, as inclusive of derivatives or analogues thereof.

---

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear     ( i i ) MOLECULE TYPE: Genomic DNA     ( i i i ) HYPOTHETICAL: NO     ( i v ) ANTI-SENSE: NO     ( v ) FRAGMENT TYPE:

( v i ) ORIGINAL SOURCE:

( i x ) FEATURE:
        ( A ) NAME/KEY: Other
        ( B ) LOCATION: 1...31
        ( D ) OTHER INFORMATION: Primer 1

( x i ) SEQUENCE DESCRIPTION: SEQ ID NO:1:

GTTAGAAAAC GTAGAAGAGA ATGGCCACAG C         31

( 2 ) INFORMATION FOR SEQ ID NO:2:

( i ) SEQUENCE CHARACTERISTICS:
    ( A ) LENGTH: 169 base pairs
    ( B ) TYPE: nucleic acid
    ( C ) STRANDEDNESS: double
    ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
    ( A ) NAME/KEY: Other
    ( B ) LOCATION: 1...57
    ( D ) OTHER INFORMATION: Insertion- sequence-like
        element ( x i ) SEQUENCE DESCRIPTION: SEQ ID NO:2:

```
GAATGGTTGG  TAAAATGTTA  GAAAACGTAG  AAGAGAATGG  CCACAGCTTA  AAAAATGTAT        60
TATTACATTC  TGATCAAGGA  TGACAATACA  CTCATCAAGA  TTATATTGAT  TATTTGAAAG       120
AAAAACAAAC  AACTCAAAGC  ATGTCAAGAA  AGGGAAATTG  TTTAGACAA                    169
```

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: Genomic DNA     ( i i i ) HYPOTHETICAL: NO     ( i v ) ANTI-SENSE: NO     ( v ) FRAGMENT TYPE:

( v i ) ORIGINAL SOURCE:

( i x ) FEATURE:
        ( A ) NAME/KEY: Other
        ( B ) LOCATION: 1...23
        ( D ) OTHER INFORMATION: SNAAC Capture Probe
        ( A ) NAME/KEY: Other
        ( B ) LOCATION: 20...23
        ( D ) OTHER INFORMATION: Non- hybridising 3'-end     ( x i ) SEQUENCE DESCRIPTION: SEQ ID NO:3:

```
CATTCTGATC  AAGGATGACT  ATT                                                   23
```

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: Genomic DNA     ( i i i ) HYPOTHETICAL: NO     ( i v ) ANTI-SENSE: NO     ( v ) FRAGMENT TYPE:

( v i ) ORIGINAL SOURCE:

```
(ix) FEATURE:
    (A) NAME/KEY: Other
    (B) LOCATION: 1...29
    (D) OTHER INFORMATION: Biotinyl- Primer 2

(xi) SEQUENCE DESCRIPTION: SEQ ID NO:4:

GTTTGTTGAG TTTCGTACAG TTCTTTCCC                                                29
```

The claims defining the invention are as follows:

We claim:

1. A method for detecting a target nucleic acid sequence, which method involves amplification and detection in the same reaction vessel and comprises:
    (a) amplification of the target nucleic acid sequence in a vessel which is provided with a solid phase capture probe comprising a nucleic acid sequence which hybridises to at least a portion of the said amplified target nucleic acid sequence, said capture probe not participating in nucleic acid sequence amplification processes, and said vessel being thermally stable, chemically derivatizable and thin-walled:
    (b) bringing a sample suspected of comprising said amplified target nucleic acid sequence into contact with said capture probe under conditions which allow said amplified target nucleic acid sequence to be bound by said capture probe; and
    (c) detecting the presence of bound amplified target nucleic acid sequence.

2. The method of claim 1, wherein the capture probe is attached to an inside surface of a reaction vessel or to a solid support which is immersible into a reaction vessel.

3. The method of claim 2, wherein the capture probe is attached to a dipstick, paramagnetic or non-paramagnetic beads, or an inside surface of a test tube, a well of a microtitre tray or modified microtitre tray lid with sections which are immersed or immersible into the reaction vessel.

4. The method of claim 1, wherein the target nucleic acid sequence is subjected to an amplification process.

5. The method of claim 4, wherein said amplification process is polymerase chain reaction; ligase chain reaction; nucleic acid sequence based amplification Q replicase dependent amplification or strand displacement amplification.

6. The method of claim 1, wherein said capture probe comprises an amplification blocking group or groups.

7. The method of claim 6, wherein the blocking group or groups comprise a 3'-sequence of a 5'-sequence which does not hybridise to the amplified target nucleic acid sequence; a 3'-dideoxyribonucleotide or a 3'-terminus linked to the solid support.

8. The method of claim 1, wherein the 3'-terminus of the said capture probe is attached to the solid support.

9. The method of claim 1, wherein the 5'-terminus of the said capture probe is attached to the solid support.

10. The method of claim 1, wherein the 5'-terminus of the said capture probe does not comprise a 5'-phosphate group.

11. The method of claim 1, wherein the capture probe is linked through one terminus to a solid support and modified at the other terminus by any one of the preceding claims.

12. The method of claim 1, wherein said capture probe comprises a nucleic acid sequence which hybridises to at least a portion of said amplified target nucleic acid sequence a nucleic acid spacer arm between the point of attachment to a solid phase linker which is, in turn, attached to the solid support.

13. The method of claim 1, wherein said bound amplified target nucleic acid sequence is detected by means of a label incorporated therein.

14. The method of claim 13, wherein said detectable label is selected from the group consisting of florescent labels; time resolved fluorescent labels; biotin; avidin; streptavidin; radiolabels; enzymes; dyes and rare earth metals.

15. The method of claim 1, wherein the amplified target nucleic acid sequence is selected from the group consisting of nucleic acid sequences specific to species of microorganisms; nucleic acid sequences characteristic of or associated with individuals, genetic disorders or diseases and nucleic acid sequences determinant of tissue type, sex or taxonomic classification.

16. The method of claim 1, when utilised in a forensic application; for maternity or parental testing; or in quality control in agriculture, horticulture or the food or pharmaceutical industries.

17. An assay system or kit, for detecting a target nucleic acid sequence in a sample suspected of comprising said target nucleic acid sequence, comprising:
    (a) a capture probe comprising a nucleic acid sequence which hybridises to at least a portion of said amplified target nucleic acid sequence, said capture probe being immobilized on a solid phase support which forms a part of or is insertable into a container for the sample, said container being thermally stable, chemically derivatizable and thin-walled, and wherein said capture probe does not participate in standard nucleic acid sequence amplification processes,
    (b) reagents for amplification of said target nucleic acid sequence, and
    (c) means for detecting said target nucleic acid sequence, when bound by said capture probe in said container.

18. The assay system or kit of claim 17, wherein said solid phase support is a dipstick; paramagnetic or non-paramagnetic beads; or an inside surface of a well of a microtitre tray, a test tube or a microtitre tray lid with sections that are immersed or immersible into the reaction vessel.

19. The assay system or kit of claim 17, wherein the reagents for amplification of said target nucleic acid sequence are those for use in polymerase chain reaction, ligase chain reaction, nucleic acid sequence based amplification, Q replicase dependent amplification or strand displacement amplification.

20. The assay system or kit of claim 1, further comprising means for incorporating a detectable label in the bound target nucleic acid sequence.

21. The assay system or kit of claim 20, said detectable label is selected from the group consisting of fluorescent labels, time resolved fluorescent labels, biotin, avidin, streptavidin, radiolabels, enzymes, dyes, intercalators and rare earth metals.

22. The assay system or kit of claim 1, wherein the target nucleic acid sequence is selected from the group consisting of nucleic acid sequences specific to species of microorganisms, nucleic acid sequences characteristic of or associated with individuals, genetic disorders or disease and nucleic acid sequences determinant of tissue type, sex or taxonomic classification.

23. The assay system or kit of claim 1, adapted for use in a forensic application, for maternity or paternity testing, or in quality control in agriculture, horticulture or the food or pharmaceutical industry.

* * * * *